United States Patent
Shudo (10) Patent No.: US 8,080,261 B2
(45) Date of Patent: *Dec. 20, 2011

(54) 1-CHLORO-2,4-DINITROBENZENE NON-AQUEOUS GEL COMPOSITIONS AND METHODS FOR USING THE SAME

(75) Inventor: Jutaro Shudo, San Jose, CA (US)

(73) Assignee: Teikoku Pharma USA, Inc., San Jose, CA (US)

(*) Notice: Subject to any disclaimer, the term of this patent is extended or adjusted under 35 U.S.C. 154(b) by 1300 days.

This patent is subject to a terminal disclaimer.

(21) Appl. No.: 11/270,884

(22) Filed: Nov. 8, 2005

(65) Prior Publication Data

US 2006/0111451 A1 May 25, 2006

Related U.S. Application Data

(63) Continuation-in-part of application No. 11/229,035, filed on Sep. 15, 2005.

(60) Provisional application No. 60/615,320, filed on Sep. 30, 2004.

(51) Int. Cl.
- A61F 13/00 (2006.01)
- A61F 13/02 (2006.01)
- A61K 9/70 (2006.01)
- A61L 15/16 (2006.01)

(52) U.S. Cl. ............ 424/449; 424/448; 424/443

(58) Field of Classification Search .......... 424/449, 424/448, 443
See application file for complete search history.

(56) References Cited

U.S. PATENT DOCUMENTS

| | | | | |
|---|---|---|---|---|
| 5,304,379 | A | * | 4/1994 | Cormier et al. ........... 424/449 |
| 5,597,576 | A | * | 1/1997 | Genova et al. ........... 424/401 |
| 5,676,968 | A | * | 10/1997 | Lipp et al. ........... 424/448 |
| 5,846,559 | A | | 12/1998 | Hopp |
| 6,455,586 | B1 | | 9/2002 | Kaplan et al. |
| 6,761,900 | B2 | | 7/2004 | Shudo et al. |
| 2003/0221457 | A1 | | 12/2003 | Cline et al. |
| 2003/0221458 | A1 | | 12/2003 | Cline et al. |
| 2005/0284820 | A1 | | 12/2005 | Luka |
| 2005/0288409 | A1 | | 12/2005 | Charbonneau et al. |

FOREIGN PATENT DOCUMENTS

| WO | WO 02/072081 | 9/2002 |
|---|---|---|
| WO | 2004/037314 | 5/2004 |

OTHER PUBLICATIONS

Stricker et al. "Dendritic Cells and Dinitrochlorobenzene (DNCB): A New Treatment Approach to AIDS." Immunology Letters (1991) 29:191-196.

Stricker et al. "Pilot study of Topical Dinitrochlorobenzene (DNCB) in Human Immuno Deficiency Virus Infection," Immunology Letters (1993) 36:1-6.

(Continued)

Primary Examiner — Isis Ghali
(74) Attorney, Agent, or Firm — Bozicevic, Field & Francis LLP; Bret E. Field (57) ABSTRACT

Gel compositions that contain 1-dichloro-2,4-dinitrobenzene (DNCB) are provided. Embodiments of the subject gel compositions include DNCB, an organic solvent and a viscosity agent, wherein the organic solvent and viscosity agent are inert with respect to the DNCB. Also provided are methods for using the subject compositions and kits for use in practicing the subject methods.

34 Claims, 2 Drawing Sheets

OTHER PUBLICATIONS

Stricker et al. "Topical Dinitrochlorobenzene in HIV Disease," J. Am. Acad Dermatol. (1993) 28:796-797.

Stricker et al. "Clinical and Immunologic Evaluation of HIV-Infected Patients Treated with Dinitrochlorobenzene," J. Am. Acad Dermatol. (1994) 31:462-466.

Stricker et al. "Improved Results of Delayed-Type Hypersensitivity Skin Testing in HIV-Infected Patients Treated with Topical Dinitrochlorobenzene," *J. Acad Dermatol.* (1995) 33:608-611.

Stricker and Goldberg "Safety of Topical Dinitrochlorbenzene," The Lancet (1995) vol. 346 pp. 1293.

Stricker et al. "Improved Results of Delayed-Type Hypersensitivity Skin Testing in HIV-Infected Patients Treated with Topical Dinitrochlorobenzene," J. Am. Acad Dermatol (1996) 35:491-493.

Stricker et al. "Decrease in Viral Load Associated with Topical Dinitrochlorobenzene Therapy in HIV Disease," Res Virol. (1997) 148:343-348.

Traub et al. "Topical Immune Modulation with Dinitrochlorobenzene (DNCB) in HIV Disease: A Controlled Trial from Brazil," Dermatology (1997) 195:369-373.

Stricker et al. "Topical Immune Modulation (TIM): A Novel Approach to the Immunotherapy of Systemic Disease," Immunology Letters (1997) 59:145-150.

Oracion et al. "DNCB Treatment of HIV-Infected Patients Leads to Beneficial Immunologic Outcomes, Reduced Viral Load, and Improved Measures of Quality-of-Life," J. Invest Dermatol. (1998) 110:476.

\* cited by examiner

1-CHLORO-2,4-DINITROBENZENE NON-AQUEOUS GEL COMPOSITIONS AND METHODS FOR USING THE SAME

CROSS-REFERENCE TO RELATED APPLICATIONS

This application is a continuation-in-part of application Ser. No. 11/229,035, filed on Sep. 15, 2005, which pursuant to 35 U.S.C. §119(e), claims priority to the filing date of the U.S. Provisional Patent Application Ser. No. 60/615,320 filed Sep. 30, 2004, the disclosure of which is herein incorporated by reference.

BACKGROUND OF THE INVENTION

The number of Human Immunodeficiency Virus (HIV) patients worldwide have been increasing rapidly in recent years, and is said to be approximately 38 million (UNAIDS; end of 2003). Against this backdrop, there is a rush to develop a vaccine for HIV. However, because of the mutation of the configuration of the virus following infection, an accurate vaccine has not yet been found. In addition, although many therapeutic medications for HIV have been developed, none completely cure HIV. Furthermore, current AIDS drugs (protease inhibitors, non-nucleoside reverse transcriptase inhibitors, nucleoside reverse transcriptase inhibitors, etc.) employ complex techniques. Long-term administration of these agents causes patients to suffer persistent adverse events, such as anemia, peripheral neuritis, pancreatitis, nausea, and headaches. Also, the possibility of long-term administration resulting in drug resistance cannot be ruled out. Yet another disadvantage of current treatment modalities is cost, in that current therapeutic medications for HIV are extremely expensive, often ranging between $15,000 to $20,000 per person per year, which necessarily limits patient access.

One type of agent that represents an effective alternative to current HIV treatment modalities is the delayed-type hypersensitivity (DTH) inducing agent, which type of agent has been researched as an immunomodulator that elicits immunological response in HIV patients by increasing the activity of the immune system cells in the body. Delayed-type hypersensitivity inducers are substances that induce Type 4 hypersensitivity when they come into contact with human skin, and they include trinitrobenzene sulfonic acid, picryl chloride (PC), 2,4-dinitrofluorobenzene (DNFB), and 1-chloro-2,4-dinitrobenzene (DNCB). Of these, DNCB has been widely used in the treatment of HIV and in immunological research, and the present invention focuses on DNCB as a DTH inducer in many embodiments, as described in greater detail below.

SUMMARY OF THE INVENTION

Gel compositions that contain 1-dichloro-2,4-dinitrobenzene (DNCB) are provided. Embodiments of the subject gel compositions include DNCB, an organic solvent and a viscosity agent, wherein the organic solvent and viscosity agent are inert with respect to the DNCB. Methods of administering DNCB to a subject are also provided. Embodiments include contacting a DNCB gel composition according to the subject invention to a skin surface of a subject and maintaining the composition at the skin surface for a period of time sufficient for DNCB to be administered to the subject. Also provided are kits for use with the subject methods. Embodiments of the subject kits include a DNCB gel composition according to the subject invention and instructions for using the composition.

DETAILED DESCRIPTION OF THE INVENTION

Gel compositions that contain 1-dichloro-2,4-dinitrobenzene (DNCB) are provided. Embodiments of the subject gel compositions include DNCB, an organic solvent and a viscosity agent, wherein the organic solvent and viscosity agent are inert with respect to the DNCB. Methods of administering DNCB to a subject are also provided. Embodiments include contacting a DNCB gel composition according to the subject invention to a skin surface of a subject and maintaining the composition at the skin surface for a period of time sufficient for DNCB to be administered to the subject. Also provided are kits for use with the subject methods. Embodiments of the subject kits include a DNCB gel composition according to the subject invention and instructions for using the composition. The subject invention finds use in a variety of applications where the administration of DNCB is desired, where embodiments include treating a subject for an immunocompromising disease and is particularly suited for use in the treatment of HIV associated disease conditions, e.g., AIDS.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

In further describing the subject invention, the subject gel compositions are described first in greater detail, followed by a review of representative methods and applications in which the gel compositions find use, as well as a review of representative kits that include the subject gel compositions.

DNCB Gel Compositions

As summarized above, the subject invention is directed to gel compositions that include DNCB. By "gel composition" is meant a colloid in a more solid form than a sol. Embodiments of the subject invention include DNCB, an organic solvent and a viscosity agent, wherein the organic solvent and viscosity agent are inert with respect to the DNCB.

A feature of the subject DNCB gel compositions is that the compositions are storage stable. By storage stable is meant that the compositions may be stored at elevated temperatures and humidity for extended periods of time without substantially decreasing the activity of the DNCB active agent. In representative embodiments, the subject compositions are stable for at least about 2 months, such as at least about 4 months, including at least about 6 months or longer, e.g., at least about 1 year, at least about 1.5 years, etc., when maintained at 40° C. and 75% humidity. By the phrase "without substantially decreasing the activity of the DNCB active agent" is meant that at the end of the storage period, there is less than about 5% reduction in activity of the DNCB compared to the beginning of the storage period, as determined using the protocol reported in the Experimental Section, below, e.g., less than about 5%.

The amount of DNCB agent that is present in a given composition is an amount sufficient to administer to a subject an effective amount of the agent when applied to a skin surface of the subject, as described in greater detail below. In certain embodiments, the amount of DNCB present may range from about 0.001% to about 10.0% (w/w) or more (e.g., about 15.0%), e.g., from about 0.05% to about 10.0% (w/w), e.g., from about 0.1% to about 5.0% (w/w), e.g., from about 0.2% to about 3.0% (w/w) of the gel composition.

Embodiments of the subject DNCB gel compositions include one or more organic solvents and a viscosity agent. In general, the organic solvent(s) and viscosity agent are inert with respect to the DNCB. By "inert" is meant that the referenced solvent or viscosity agent produces less than about 5% reduction in activity of the DNCB over a period of time ranging from about 1 month to about 1 year, e.g., from about 2 months to about 9 months, e.g., from about 3 months to about 6 months, at 40° Celsius, as determined using the protocol reported in the Experimental Section below.

As such, the one or more organic solvents are selected so as to be inert with respect to the DNCB. In certain embodiments, the organic solvent(s) is a non-volatile organic solvent. By "non-volatile" is meant the solvent does not substantially evaporate when exposed to the atmosphere under standard pressure/temperature conditions, e.g., when contacted with a skin surface of a subject, for at least about 4 hours or more, e.g., about 6 hours or more, e.g., 8 hours or more at a temperature of about 40° Celsius or less.

Organic solvents that may be used include organic solvents that are free of metallic ions and/or organic solvents that are free of hydroxyl groups and/or organic solvent that are ester organic solvents. For example, an organic solvent may be a non-volatile organic solvent that is free of metallic ions and/or a non-volatile organic solvent that is free of hydroxyl groups and/or a non-volatile ester organic solvent. In certain embodiments, an organic solvent may a solvent that possesses at least two of the above-described properties (e.g., both metallic ion free and hydroxyl group free), where in certain embodiments an organic solvent may posses all three properties (i.e., metallic ion free, hydroxyl group free and is an ester).

Examples of non-volatile organic solvents that may be used in the subject invention include, but are not limited to, ester nonvolatile solvents such as diisopropyl adipate, isopropyl myristate, propylene carbonate and diethyl sebacate and organic solvents that do not contain hydroxyl groups or metallic ions such as diethyltoluamide, crotamiton and paraffin.

The organic solvent may be a single organic solvent component or may be a combination of two or more solvent components, e.g., a combination or any two or more solvents noted above. For example, a composition may include isopropyl myristate and diethyl sebacate organic solvents.

The amount of organic solvent present will vary depending on the particular solvent(s) used. In certain embodiments, the amount of organic solvent may range from about 0.001% to about 99.999% (w/w), e.g., from about 1% to about 98% (w/w), e.g., from about 3% to about 98%, e.g., from about 5% to about 95% (w/w), e.g., from about 7% to about 93% (w/w) of the gel composition.

Embodiments also include a viscosity agent that is inert with respect to the DNCB in the composition. Of particular interest are viscosity agents that stabilize the viscosity of the subject DNCB compositions over a range of temperatures, e.g., viscosity agents that minimize the extent of the decrease in viscosity as the temperature is raised, minimizes the extent of the increase in viscosity as the temperature is lowered, or both. Thus, a viscosity agent may be selected to ameliorate the change of viscosity of a composition with changes in temperature. Of interest are viscosity agents that stabilize the subject DNCB compositions at temperatures at which the gel composition may be subjected, e.g., low or high temperatures such as during transport and/or storage of the gel composition. For example, viscosity agents that maintain stability of DNCB at high temperatures, e.g., about 40° C., may be used. A representative viscosity agent that may be used includes, but is not limited to, silica, with which DNCB is stable at temperatures of up to as high as about 40° C.

The amount of viscosity agent present in the gel will vary depending on the particular gel components, and in representative embodiments is chosen to be sufficient to impart the desired viscosity to the composition. In certain embodiments, the amount of viscosity agent may range from 0.001% to about 50% (w/w), e.g., from about 0.01% to about 40% (w/w), e.g., from about 0.05% to about 35% (w/w), e.g., from about 0.1% to about 30% (w/w) of the gel composition.

In certain embodiments, a subject DNCB gel composition may be present on a surface of a topical patch delivery vehicle. By "topical patch delivery vehicle" is meant a structure that is configured to be used in the delivery of a composition to a skin site of a subject. Representative topical patch delivery vehicles include a structure for retaining or holding a gel composition. For example, a topical patch delivery vehicle may include a gel composition retaining layer present on a support. The support or backing may be made of a flexible material which is capable of accommodating the movement of human body. By "flexible" is meant that the support may be substantially bent or folded without breaking, tearing, ripping, etc.

The support may be porous or non-porous. For example, embodiments include non-porous supports or supports that are impermeable to the DNCB composition. The impermeability of the support to the DNCB gel composition may enhance or increase the penetration of the DNCB into the skin.

Any suitable material may be used for a support. Representative support materials of interest include, but are not limited to, various woven fabrics, non-woven fabrics, spandex, flannel, films such as urethane and polyurethane films, PET films, PP films, polyethylene film, polyethylene glycol terephthalate film, polyvinyl chloride film, ethylene-vinyl acetate copolymer film, polyurethane film, and the like. The support may be a composite, (e.g., using any of the materials described above), i.e., a composition comprised of unlike materials. The composite may be a block composite, e.g., an A-B-A block composite, an A-B-C block composite, or the like. Alternatively, the composite may be a heterogeneous combination of materials, i.e., in which the materials are distinct separate phases; or it may be a homogeneous combination of unlike materials. As used herein, the term "composite" is used to include a "laminate" composite. A "laminate" refers to a composite material formed from several different bonded layers of identical or different materials.

The gel composition retaining layer may be any material configured to retain an amount of gel composition, e.g., may be gauze, nonwoven cloth, laminated fabric, and the like.

The topical patch delivery vehicle may also include an adhesive. The adhesive may be positioned at least between the support and the gel composition retaining later and may cover an entire surface of the support. Any suitable adhesive may be used. For example, the adhesive may be a polymer, e.g., such as is commonly used in external preparations, such as an SIS (styrene-isoprene-styrene) copolymer or an SBS (styrene-butadiene-styrene) copolymer.

A release film may also be present over the DNCB gel retaining layer for protection of the retaining layer and other components of the topical patch delivery vehicle from the environment. The release film may be any convenient material, where representative release films include polyesters, such as PET or PP, and the like.

The shape of a topical patch delivery may vary, where exemplary shapes include square, rectangle, oval, circle, etc., as well as complex or irregular shapes. The size of a topical patch delivery vehicle may also vary, where in certain embodiments the size may range from about 1 to about 200 cm$^2$, e.g., from about 50 to about 150 cm$^2$, e.g., about 100 cm$^2$. In certain embodiments, a topical patch delivery vehicle may be provided to a subject in a specific size and/or shape, but which may be re-shaped or re-sized by the user, e.g., cut or separated along perforated markings, to fit to a particular application site on the user's body.

Figure 1:
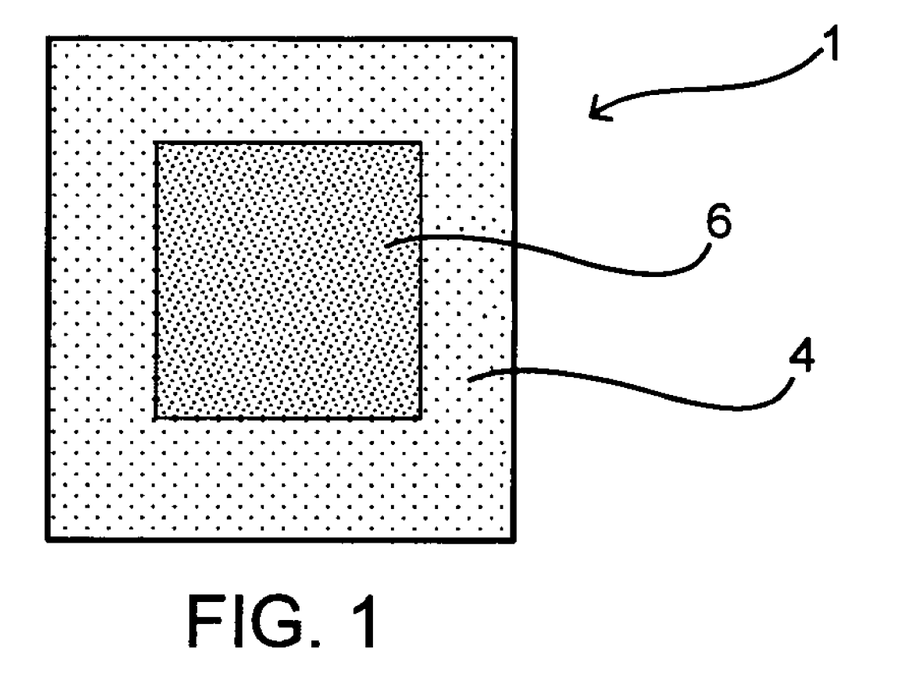
FIG. 1 shows a top view of an exemplary embodiment of a topical patch delivery vehicle according to the subject invention.
Figure 2:
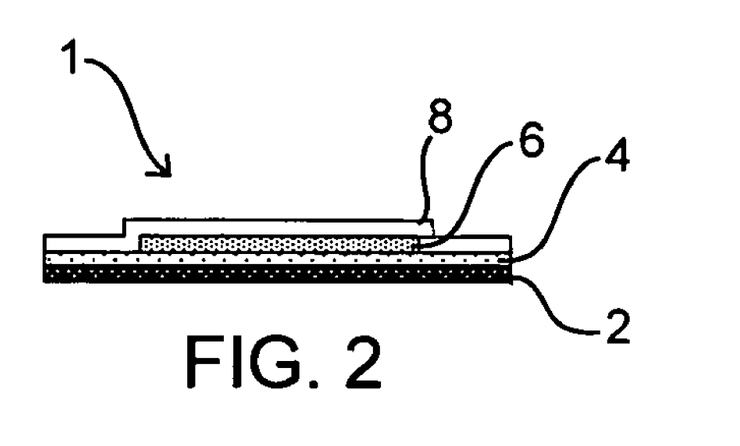
FIG. 2 shows a side view of the topical patch delivery vehicle of FIG. 1.

FIG. 1 shows a top view of a topical patch delivery vehicle 1 and FIG. 2 shows a side view of the topical patch delivery vehicle of FIG. 1. Topical Patch delivery vehicle 1 includes support 2, adhesive layer 4, gel retaining layer 6 and release liner 8. As noted above, one or more of these components may be omitted in certain embodiments.

In many embodiments, the DNCB gel composition may be present in a sealed package. The packaging material is capable of preventing passage of moisture, oxygen and other agents, i.e., the package includes a moisture/oxygen barrier material. Any suitable packaging material(s) may be employed, where packaging materials of interest include those that include polyacrylonitrile. For example, packaging material including a polyacrylonitrile layer may be used. Other materials that may be used include, but are not limited to, metallic materials, polyester materials, and the like. For example, a DNCB gel composition package may include a metallic layer, e.g., an aluminum layer, and/or a polyester layer, e.g., a PET layer, PP layer, and the like. In certain embodiments, a DNCB gel composition package is a laminate, where in certain embodiments the laminate includes a material that includes polyacrylonitrile. For example, packaging may be in the form of a laminate having a polyacrylonitrile film layer, a metallic film layer (e.g., an aluminum layer) and a polyester film layer (e.g., a layer of PET or PP).

In embodiments in which the package is a laminate of layers, layers may have the same or different thicknesses, where the thickness of each layer may range from about 3 μm to about 20 μm, e.g., from about 5 μm to 15 μm. The total thickness of a package may range from about 6 μm to about 60 μm, e.g., from about 15 μm to about 45 μm. The packaging may be any suitable shape, e.g., regular geometric shapes such as square, rectangular, circular, oval, etc., or may be an irregular or complex shape.

A gel composition may be sealed inside a package in any suitable manner. For example, any opened edges of the packaging may be heat sealed together with gel composition therein, where in certain embodiments the entire perimeter of the packaging may be heat sealed to provide a sealed package, e.g., in those instances in which a package is made from two separate pieces of material that need to be joined together to provide a sealed package.

Figure 3:
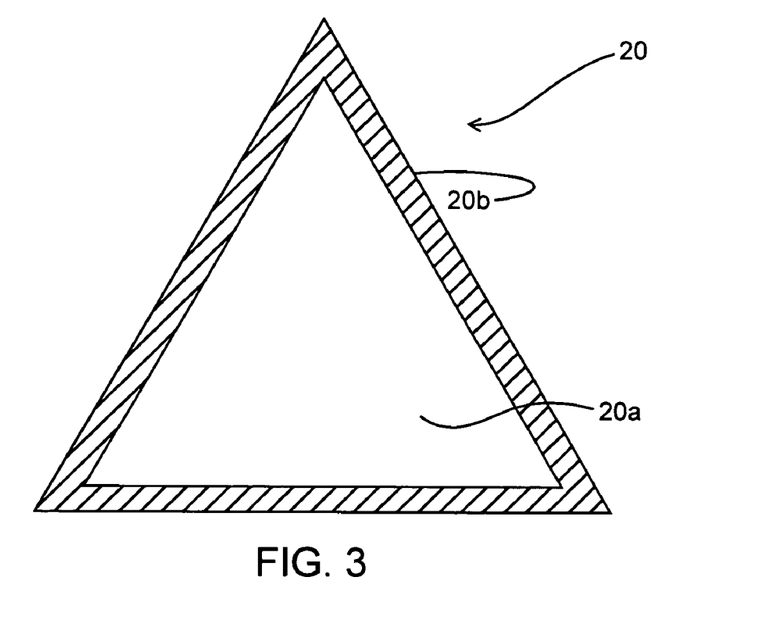
FIG. 3 shows a top view of an exemplary embodiment of packaging for sealing the subject DNCB gel compositions therein.
Figure 4:
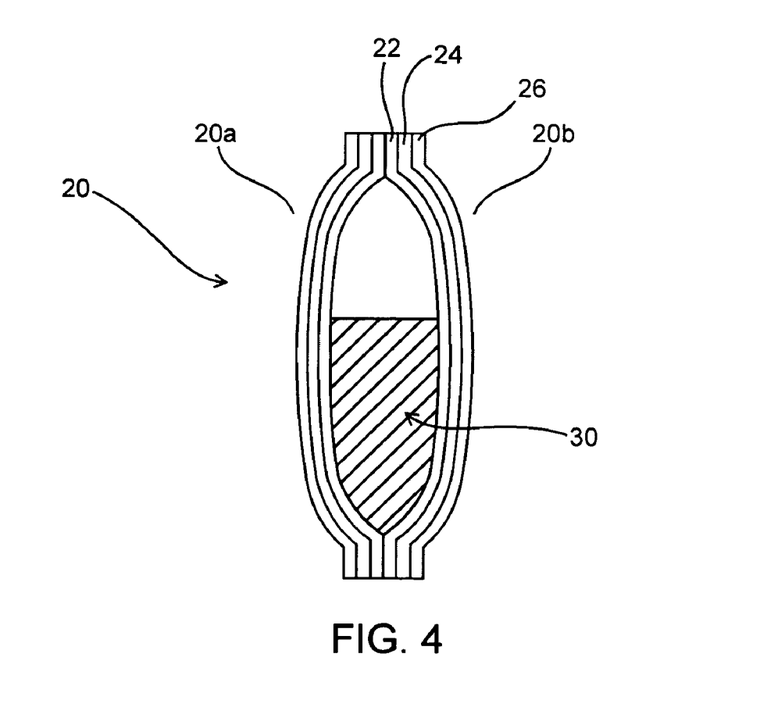
FIG. 4 shows a cross-sectional view of the sealed packaging of FIG. 3 having DNCB gel composition sealed therein.

FIG. 3 shows an exemplary embodiment of a sealed package 20 having a triangular shape. The edges of the perimeter of package 20 are heat sealed (indicated by cross-hatching) to provide a sealed package. That is, package 20 includes a first package member 20a making up first side of the package and a second package member 20b making up a second package side wherein package members 20a and 20b are heat sealed together along their edges to provide a sealed package with gel composition stored therein. FIG. 4 shows a cross-sectional view of the sealed package of FIG. 3. As shown in FIG. 4, package 20 is a laminate of 3 layers: layer 22, 24 and 26, and includes DNCB gel composition 30 heat sealed in the package. For example, layer 22 may be a polyacrylonitrile layer, layer 24 may be an aluminum film layer and layer 26 may be a polyester film layer.

The gel composition may be packaged in any suitable manner. In certain embodiments, the gel composition is packaged alone in a package. In embodiments in which a topical patch delivery vehicle is used with the application of the gel composition, the gel composition and the topical patch delivery vehicle may both be heat sealed within the same package, e.g., the gel composition may be present on the gel composition retaining later, e.g., in those embodiments where the retaining layer components are inert, as described above, to the DNCB active agent of the gel. In alternative embodiments, the gel composition and topical patch delivery vehicle are packed separately or otherwise physically separated from each other. For example, a DNCB gel composition may be heat sealed in a first package (see for example package 20 of FIG. 4) and a topical patch delivery vehicle may be heat sealed in a second package (not shown), which second package may be the same or different type of package from the first package. In use, each will be removed from its respective package.

The DNCB gel compositions may be fabricated using any convenient protocol. One convenient protocol for fabrication of the subject gel compositions includes preparing a gel composition through the uniform mixing of the aforementioned ingredients. For example, DNCB may be dissolved in an organic solvent, e.g., by adding the DNCB to the solvent while mixing or vice versa, using a mixer to uniformly blend the aforementioned ingredients. Once dissolved, the dissolved DNCB solution may then be added to another organic solvent and/or to a viscosity agent while mixing, or vice versa, using a mixer to uniformly blend the aforementioned ingredients.

This gel composition may then be packaged by heat sealing the composition in packaging material that includes polyacrylonitrile, e.g., that includes a layer of polyacrylonitrile film, to obtain a sealed DNCB gel composition.

It should be noted that the manufacturing protocols described herein are merely exemplary. Any convenient protocol that is capable of producing the subject DNCB gel composition, as described above, may be employed.

Methods of Using DNCB Gel Compositions

The subject gel compositions find use in the topical delivery of DNCB, to a subject. By "topical delivery" is meant delivery via absorption through the skin. In using the subject gel composition to topically administer DNCB to a subject, the DNCB gel composition is applied to a skin surface and maintained at the site of application for a period of time sufficient for the desired amount of DNCB to be delivered to the subject. In certain embodiments, the period of time required to deliver the desired amount of agent may be short, e.g., may not exceed about 120 minutes, e.g., may not exceed about 60 minute, e.g., may not exceed about 40 minutes. However, the period of time during which the DNCB gel composition is maintained at the application site may be, in certain embodiments, at least about 1 minute, e.g., at least about 3 minutes, e.g., at least about 5 minutes, e.g, at least about 15 minutes. In certain embodiments, the period of time may be about 15 minutes or more, e.g., 60 minutes or more, e.g., two or more hours, e.g., 3 hours or more, e.g., four hours or more, e.g., 5 hours or more, e.g., 6 hours or more, e.g., 7 hours or more, e.g., 8 hours or more, e.g., 10 hours or more, e.g., 11 hours or more, e.g., 12 hours or more, where in certain embodiments the period of time does not exceed about 8 hours. For example, the time period may range from about 5 minutes to about 7 hours, e.g., from about 15 minutes to about 4 hours. In other embodiments, the period of time does not exceed about 12 hours. For example, the time period may range from about 5 minutes to about 11 hours, e.g., from about 15 minutes to about 7 hours.

The DNCB gel compositions may be administered to any convenient topical site. Topical sites of interest include, but are not limited to: arms, leg, torso, neck, scalp, etc. The surface area that is covered by DNCB gel composition following application must be sufficient to provide for the desired amount of agent administration, and in certain embodiments may range from about 1 to about 200 cm$^2$, e.g., from about 50 to about 150 cm$^2$, e.g., about 100 cm$^2$. In practicing the subject methods, a DNCB gel composition may be applied a single time or a plurality of times over a given time period at the same or different application site, e.g., the course of the disease condition being treated, where the dosing schedule when a plurality of patches are administered over a given time period may be daily, weekly, biweekly, monthly, etc. In certain embodiments, the DNCB gel compositions of the subject invention need only be applied to a skin surface of a subject one time per week, e.g., where it is maintained at the application site for a period of time that falls within the ranges described herein, e.g., a period of time that does not exceed about 8 hours, e.g., a period of time that may range from about 5 minutes to about 7 hours, e.g., from about 15 minutes to about 4 hours, e.g., a period of time that does not exceed about 12 hours, e.g., a period of time that may range from about 5 minutes to about 11 hours, e.g., from about 15 minutes to about 7 hours.

In certain embodiments, a DNCB gel composition of the invention is applied to a topical site of subject and then covered with a topical patch delivery vehicle, where the topical patch delivery vehicle then remains in place, adhesively contacted to the skin, for a period of time sufficient to administer an amount of DNCB to the subject. In certain other embodiments, DNCB gel composition may be first contacted with the DNCB gel retaining layer present on a support of a topical patch delivery vehicle, which DNCB gel composition-containing delivery vehicle may then be applied to a topical site of subject and which may then remain in place at the application site, adhesively contacted to the skin, for a period of time sufficient to administer an amount of DNCB to the subject.

For example, a topical patch delivery vehicle may be removed from any packaging that may be present, and then the protective layer, if present, may be removed from the topical patch delivery vehicle, thereby exposing the gel composition retaining layer. In one embodiment, DCNB gel composition may be removed from its packaging and applied directly to a skin surface of a subject. The topical patch delivery vehicle may then be positioned over the topically applied DNCB composition to occlude the DNCB composition. In certain embodiments, DNCB composition may be removed from its packaging and applied to the gel composition retaining layer of the topical patch delivery vehicle, which may then be contacted with a skin surface of a subject.

Once a sufficient amount of time has elapsed, the topical patch delivery vehicle may be removed from the application site. Embodiments include topical patch delivery vehicles adapted to be easily and non-traumatically removed from an application site by simply peeling the topical patch delivery vehicle away from the site.

Utility

The above described DNCB gel compositions and methods find use in any application in which the administration of DNCB to a subject is desired. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

In certain embodiments, the subject methods find use in the treatment of a disease condition. By treatment is meant at least an amelioration of the symptoms associated with the pathological condition afflicting the subject, where amelioration is used in a broad sense to refer to at least a reduction in the magnitude of a parameter, e.g. symptom, associated with the pathological condition being treated, such as viral load or side effects associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition. As such, treatment includes both curing and managing a disease condition.

In certain embodiments, the disease condition that is treated according to the subject methods is one that is a chronic disease. Chronic diseases of interest include, but are not limited to: hepatitis, chronic fatigue syndrome, systemic lupus erythematosus, leprosy, leishmaniasis, diseases associated with the presence of intracellular pathogenic agents (e.g., viruses, bacteria), such as cytomegalovirus, Candida, Cryptococcus, Penumocystis carinii, and the like.

Of interest is the use of the subject methods in the treatment, e.g., management, of immunocompromising disease conditions, and particularly HIV associated disease conditions, e.g., AIDS. Treatment in the context of HIV associated diseases means improvement of quality of life, e.g., via reduction in one or more symptoms, the occurrence of opportunistic infections, etc. In terms of quantifiable parameters associated with HIV disease conditions, the subject invention finds use in reducing viral load and/or increasing the population of natural killer cells, while varying the population of at least one of CD4 cells and CD8 cells. Such changes in quantifiable parameters may be achievable with application times that do not exceed about 8 hours in length.

Kits

Also provided are kits, where the subject kits at least include DNCB gel composition, as described above. The subject DNCB gel composition in the kits may be present in a package, as described above. Kits may include DNCB gel composition in an amount suitable for a single application or multiple applications. In instances in which DNCB gel composition is present in a kit in an amount sufficient for more than one application, multiple packages, as described above, may be provided with each containing an amount of DNCB gel composition for a single application.

Kits may also include one or more topical patch delivery vehicles which may be packaged together with DNCB gel compositions. For example, a DNCB gel composition may be packaged separately from the topical patch delivery vehicle(s), i.e., in the same kit, but physically separated. For example a first package may include DNCB gel composition sealed therein and a second package may include a topical patch delivery vehicle sealed therein. In instances in which more than one topical patch delivery vehicle is present in a kit, with or without DNCB gel composition already contacted therewith, each topical patch delivery vehicle may be present in separate, individual package from other topical patch delivery vehicles.

The subject kits may also include instructions for how to use the DNCB compositions in methods of DNCB delivery to a subject and/or how to use topical patch delivery vehicles whether provided in the kit or not. The instructions may include information about where to apply the DNCB gel composition, dosing schedules etc., and/or how to use DNCB gel compositions with topical patch delivery vehicles, e.g., if provided separately. In certain embodiments, the subject kits include instructions on how to use the DNCB gel compositions to treat a particular disease condition, e.g., HIV. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g. CD-ROM, diskette, etc.

The following practical and comparative examples are offered by way of illustration and not by way of limitation.

EXAMPLES

Practical and comparative examples are given below, but the manufacturing method is not limited thereby.

Gel Composition Stability

Practical Example 1

10% DNCB/44% isopropyl myristate/40% diethyl sebacate/6% silica

DNCB 20 g (w/v) was uniformly dissolved in isopropyl myristate 88 g (w/v). 80 g(w/v) diethyl sebacate was added to the DNCB/isopropyl myristate solution, and then 12 g (w/v) silica was added to the DNCB/isopropyl myristate/diethyl sebacate solution, after which the resulting DNCB gel was packaged in 3 inch triangle envelopes (inner layer: polyacrylonitrile, intermediate layer: aluminum, outer layer: polyester) in quantities of 2 g gel composition per package. The envelopes were then completely heat-sealed, and stored in a thermostatic chamber at 40° C. and a humidity of 75%.

Practical Example 2

10% DNCB/83% Crotamiton/7% silica

DNCB 20 g (w/v) was uniformly dissolved in crotamiton 166 g (w/v). Silica 14 g(w/v) was added to the DNCB/crotamiton solution, after which the resulting DNCB gel was packaged in 3 inch triangle envelopes (inner layer: polyacrylonitrile, intermediate layer: aluminum, outer layer: polyester) in quantities of 2 g of gel composition per package. The envelopes were then completely heat-sealed, and stored in a thermostatic chamber at 40° C. and a humidity of 75%.

Practical Example 3

5% DNCB/83% isopropyl myristate/12% silica

DNCB 10 g (w/v) was uniformly dissolved in isopropyl myristate 166 g (w/v). Then 24 g (w/v) silica was added to the DNCB/isopropyl myristate solution, after which the resulting DNCB gel was packaged in 3 inch triangle envelopes (inner layer: polyacrylonitrile, intermediate layer: aluminum, outer layer: polyester) in quantities of 2 g gel composition per package. The envelopes were then completely heat-sealed, and stored in a thermostatic chamber at 40° C. and a humidity of 75%.

Comparative Example 1

10% DNCB/80% Polyethyleneglycol 300/10% silica

DNCB 20 g (w/v) was uniformly dissolved in polyethyleneglycol 300 160 g (w/v). Silica 20 g(w/v) was added to the DNCB/polyethyleneglycol 300 solution, after which the resulting DNCB gel was packaged in 3 inch triangle envelopes (inner layer: polyacrylonitrile, intermediate layer: aluminum, outer layer: polyester) in quantities of 2 g gel per package. The envelopes were then completely heat-sealed, and stored in a thermostatic chamber at 40° C. and a humidity of 75%.

Comparative Example 2

10% DNCB/80% Propyleneglycol/10% Polyacrylic Acid

DNCB 20 g (w/v) was uniformly dissolved in propyleneglycol 160 g (w/v). Polyacrylic acid 20 g (w/v) was added to the DNCB/propyleneglycol solution, after which the resulting DNCB gel was packaged in 3 inch triangle envelopes (inner layer: polyacrylonitrile, intermediate layer: aluminum, outer layer: polyester) in quantities of 2 g gel per package. The envelopes were then completely heat-sealed, and stored in a thermostatic chamber at 40° C. and a humidity of 75%.

Table 1

Stability data for Practical Examples 1-3 and Comparative Examples 1-2 are provided in Table 1. Stability was determined in accordance with ICH (The International Conference on Harmonisation) guidelines. The tests were performed with a sample size of 3 (n=3) for each composition per time point and the results are expressed as the means thereof. The tests were performed in an environment of 40° C. and 75% humidity.

The results are shown as a DNCB percentage relative to the initial DNCB value.

|  | Baseline | After 1 month | After 2 months | After 4 months | After 6 months |
| --- | --- | --- | --- | --- | --- |
| Practical Example 1 | 100% | 99.8% | 98.2% | 97.2% | 97.7% |
| Practical Example 2 | 100% | 100.01% | 98.7% | 98.9% | 98.9% |
| Practical Example 3 | 100% | 99.1% | 99.0% | 97.8% | 98.1% |
| Comparative Example 1 | 100% | 97.2% | 94.8% | 88.0% | 80.4% |
| Comparative Example 2 | 100% | 95.0% | 89.7% | 78.9% | 71.1% |

Discussion

Table 1 demonstrates the stability of the DNCB gel compositions of Practical Examples 1, 2 and 3 at 40° C. and 75% humidity over a six month period and also demonstrates that the gel compositions that include the combination of DNCB, non-volatile solvent and silica showed the best stability at 40° C. and 75% humidity. It is noted that 95% or higher recovery relative to the initial value is recognize as stable pursuant to ICH stability test guidelines. In contrast, Comparative Examples 1 and 2 were demonstrated a lack of stability for the subject formulations at 40° C. and 75% humidity, because these comparative examples had the solvent and/or viscosity agent that included hydroxyl groups which could react with DNCB, thereby adversely affecting the DNCB activity. The data also demonstrate that at least six month stability may be obtained at a DNCB concentration of 10%. The stability data demonstrates that the subject DNCB gel compositions may be used in areas of high temperatures and/or high humidity, e.g., tropical regions and countries in Africa.

It is evident from the above discussion and results that the subject invention provides an important new DNCB gel composition that is highly storage stable, even under conditions of high temperature and humidity. As such, the subject invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A non-aqueous gel composition comprising:
    1-Chloro-2,4-Dinitrobenzene (DNCB);
    an organic solvent; and
    silica;
    wherein said organic solvent and silica are inert with respect to said DNCB; and
    said non-aqueous gel composition is formulated to be stored for 6 months at 40° C. and 75% humidity with less than 5% reduction in DNCB activity, wherein the gel composition is topical composition.

2. The composition of claim 1, wherein said silica is present in said composition in an amount ranging from about 0.001% to about 50% (w/w).

3. The composition of claim 1, wherein said organic solvent is a non-volatile organic solvent.

4. The composition of claim 3, wherein said non-volatile organic solvent is at least one of: a metallic ion-free non-volatile solvent, a hydroxyl group-free non-volatile solvent and an ester-comprising non-volatile organic solvent.

5. The composition of claim 4, wherein said non-volatile organic solvent is a metallic ion-free and hydroxyl group-free non-volatile organic solvent.

6. The composition of claim 5, wherein said non-volatile organic solvent is chosen from the group of: diethyltoluamide, crotamiton, and paraffin.

7. The composition of claim 4, wherein said non-volatile organic solvent is an ester-comprising non-volatile organic solvent.

8. The composition of claim 7, wherein said ester comprising non-volatile organic solvent is chosen from the group of: diisopropyl adipate, isopropyl myristate propylene carbonate and diethyl sebacate.

9. The composition of claim 1, wherein said organic solvent is present in an amount ranging from about 0.001% to about 99.999% (w/w).

10. The composition of claim 1, wherein said gel composition is present on a surface of a topical patch delivery vehicle.

11. The composition of claim 10, wherein said topical patch delivery vehicle comprises a gel composition retaining layer present on a support.

12. The composition of claim 11, wherein said topical patch delivery vehicle further comprises an adhesive layer.

13. The composition of claim 12, wherein said adhesive layer is a polymer.

14. The composition of claim 1, wherein said DNCB is present in said gel composition in an amount ranging from about 0.001 to 15.0% (w/w).

15. The composition according to claim 1, wherein said composition is present in a packaging material comprising polyacrylonitrile.

16. A non-aqueous gel composition comprising:
    1-Chloro-2,4-Dinitrobenzene (DNCB) in an amount ranging from about 0.001 to 15.0% (w/w);
    a non-volatile organic solvent that is inert with respect to said DNCB, wherein said solvent is present in an amount ranging from about 0.001% to about 99.999% (w/w); and
    silica in an amount ranging from about 0.001% to about 99.999% (w/w);

wherein said non-aqueous gel composition may be stored for 6 months at 40° C. and 75% humidity with less than 5% reduction in DNCB activity, wherein the gel composition is topical composition.

17. A method of administering DNCB to a subject, said method comprising:
contacting DNCB gel composition according to claim 1 to a skin surface of a subject; and
maintaining said composition at said skin surface for a period of time sufficient for DNCB to be administered to the subject.

18. The method according to claim 17, wherein said method comprises applying said gel composition to a gel retaining layer of a topical patch delivery vehicle prior to contacting said gel composition to said skin surface.

19. The method according to claim 17, wherein method is a method of treating a subject suffering from an immunocompromising disease.

20. The method of claim 19, wherein said immunocompromising disease is an HIV infection.

21. A kit comprising:
(a) a DNCB gel composition according to claim 1; and
(b) instructions for using said composition to administer DNCB to a subject.

22. The kit of claim 21, wherein said kit further comprises a topical patch delivery vehicle.

23. The kit according to claim 22, wherein said gel composition and said topical patch delivery vehicle are packaged separately.

24. The kit of claim 21, wherein said composition is sealed in packaging material comprising polyacrylonitrile.

25. The composition of claim 16, wherein said non-volatile organic solvent is at least one of: a metallic ion-free non-volatile solvent, a hydroxyl group-free non volatile solvent and an ester comprising non-volatile organic solvent.

26. The composition of claim 25, wherein said non-volatile solvent is a metallic ion-free and hydroxyl group-free non-volatile organic solvent.

27. The composition of claim 26, wherein said non-volatile organic solvent is chosen from the group of: diethyltoluamide, crotamiton, and paraffin.

28. The composition of claim 25, wherein said non-volatile organic solvent is an ester-comprising non-volatile organic solvent.

29. The composition of claim 28, wherein said ester comprising non-volatile organic solvent is chosen from the group of: diisopropyl adipate, isopropyl myristate propylene carbonate and diethyl sebacate.

30. The composition of claim 16, wherein said gel composition is present on a surface of a topical patch delivery vehicle.

31. The composition of claim 30, wherein said topical patch delivery vehicle comprises a gel composition retaining layer present on a support.

32. The composition of claim 31, wherein said topical patch delivery vehicle further comprises an adhesive layer.

33. The composition of claim 32, wherein said adhesive layer is a polymer.

34. The composition according to claim 16, wherein said composition is present in a packaging material comprising polyacrylonitrile.

* * * * *